US009202723B2

(12) United States Patent
Withers et al.

(10) Patent No.: US 9,202,723 B2
(45) Date of Patent: Dec. 1, 2015

(54) BRUSH WITH CANTILEVERED NODULES

(75) Inventors: Bradley S. Withers, El Dorado Hills, CA (US); Michael G. Croker, Rocklin, CA (US); Robert A. Willis, Diamond Springs, CA (US)

(73) Assignee: ILLINOIS TOOL WORKS, INC., Glenview, IL (US)

( * ) Notice: Subject to any disclaimer, the term of this patent is extended or adjusted under 35 U.S.C. 154(b) by 917 days.

(21) Appl. No.: 13/306,624

(22) Filed: Nov. 29, 2011

(65) Prior Publication Data

US 2013/0133692 A1    May 30, 2013

(51) Int. Cl.
| | |
|---|---|
| *B08B 3/00* | (2006.01) |
| *H01L 21/67* | (2006.01) |
| *A46B 9/02* | (2006.01) |
| *A46B 13/00* | (2006.01) |
| *A46D 1/00* | (2006.01) |

(52) U.S. Cl.
CPC ............ *H01L 21/67046* (2013.01); *A46B 9/02* (2013.01); *A46B 13/001* (2013.01); *A46D 1/0253* (2013.01); *A46D 1/0207* (2013.01)

(58) Field of Classification Search
None
See application file for complete search history.

(56) References Cited

U.S. PATENT DOCUMENTS

| | | | |
|---|---|---|---|
| 1,475,079 | A | 11/1923 | Miller |
| 2,691,181 | A | 10/1954 | Van Guilder |
| 3,086,241 | A | 4/1963 | Bohn |
| 4,566,911 | A | 1/1986 | Tomita et al. |
| 5,858,109 | A | 1/1999 | Hymes et al. |
| 5,901,399 | A | 5/1999 | Moinpour et al. |
| 5,921,399 | A * | 7/1999 | Bakula et al. ................ 209/272 |
| 6,299,698 | B1 | 10/2001 | Emami |
| 6,308,623 | B1 | 10/2001 | Schonberger |

(Continued)

FOREIGN PATENT DOCUMENTS

| | | |
|---|---|---|
| DE | 4126563 | 3/1992 |
| JP | 10242100 | 9/1998 |
| WO | 2011103538 | 8/2011 |

OTHER PUBLICATIONS (Weisstein, Eric W. "Pythagorean Theorem." From MathWorld—A Wolfram Web Resource. (http://mathworld.wolfram.com/PythagoreanTheorem.html), retrieved Nov. 22, 2013.

(Continued)

*Primary Examiner* — Eric Golightly
(74) *Attorney, Agent, or Firm* — Klintworth & Rozenblat IP LLC

(57) ABSTRACT

A cleaning device for cleaning substrates is provided. The device comprises a cleaning brush having an outer cleaning surface surrounding a hollow bore and positioned around a first central axis $a_1$ defining a first rotational direction $\alpha$; and a plurality of cantilevered nodules formed on the outer cleaning surface, each nodule having a mounting portion connected with the outer cleaning surface, a cleaning portion connected with the mounting portion, and a contact member for engaging the substrate. The cleaning portion extends in a first direction $D_1$ from the mounting portion to the contact member, wherein a radial direction $D_r$ is defined as extending radially from the central axis $a_1$ towards the outer cleaning surface and normal to the rotational direction $\alpha$, and wherein the first direction $D_1$ intersects with the radial direction $D_r$ at an angle $\gamma$. Angle $\gamma$ is greater than 0° and less than 180°.

10 Claims, 13 Drawing Sheets

(56) References Cited

U.S. PATENT DOCUMENTS

| | | |
|---|---|---|
| 6,502,273 B1 | 1/2003 | Mihara et al. |
| 6,598,255 B1 | 7/2003 | Gohda et al. |
| 6,802,099 B2 | 10/2004 | Murakami et al. |
| D622,920 S | 8/2010 | Bejtlich, III |
| 8,821,645 B2 | 9/2014 | Hentges |
| 2001/0022008 A1 | 9/2001 | Dickey et al. |
| 2002/0005212 A1 | 1/2002 | Beardsley et al. |
| 2004/0040576 A1 | 3/2004 | Sun et al. |
| 2005/0064712 A1 | 3/2005 | Andreas |
| 2005/0092350 A1 | 5/2005 | Buehler |
| 2006/0096049 A1 | 5/2006 | Sun et al. |
| 2006/0200921 A1 | 9/2006 | Shih et al. |
| 2006/0276108 A1 | 12/2006 | Benson |
| 2007/0181153 A1 | 8/2007 | Kobayashi et al. |
| 2007/0209126 A1 | 9/2007 | Montabaur |
| 2008/0141475 A1 | 6/2008 | Drury |
| 2008/0276394 A1 | 11/2008 | Sato |
| 2010/0043160 A1 | 2/2010 | Chen |
| 2010/0212100 A1 | 8/2010 | Ku et al. |
| 2011/0162160 A1 | 7/2011 | Whittaker |
| 2011/0182653 A1 | 7/2011 | Miller |
| 2011/0265279 A1 | 11/2011 | Kawaguchi et al. |
| 2011/0277789 A1 | 11/2011 | Benson |
| 2013/0133692 A1 | 5/2013 | Withers et al. |
| 2013/0255721 A1 | 10/2013 | Tyrrell et al. |
| 2013/0276248 A1 | 10/2013 | Majeed |
| 2013/0283553 A1 | 10/2013 | Chen et al. |
| 2013/0283556 A1 | 10/2013 | Chen et al. |

OTHER PUBLICATIONS

PCT International Search Report (Apr. 4, 2013).

\* cited by examiner

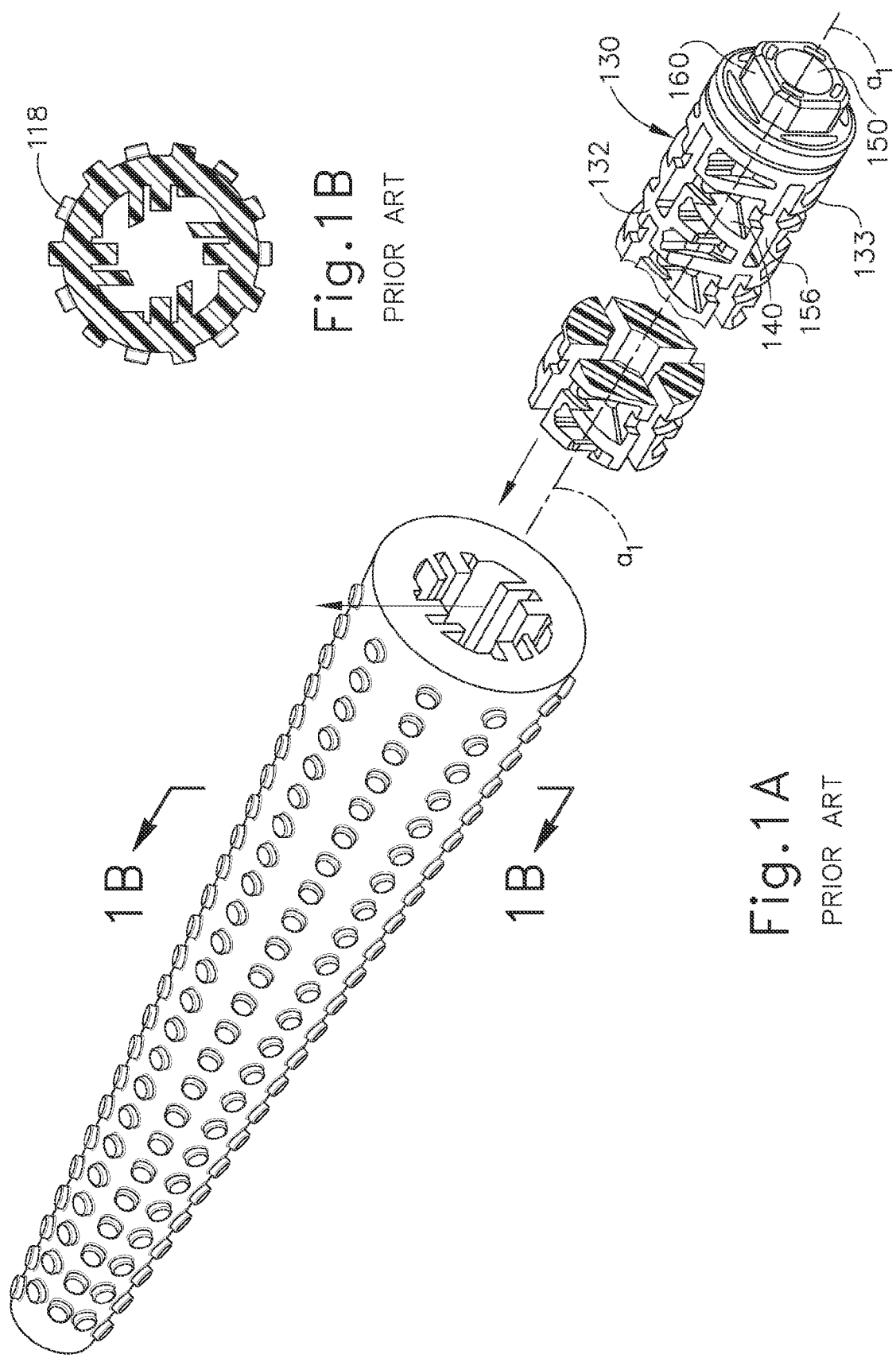

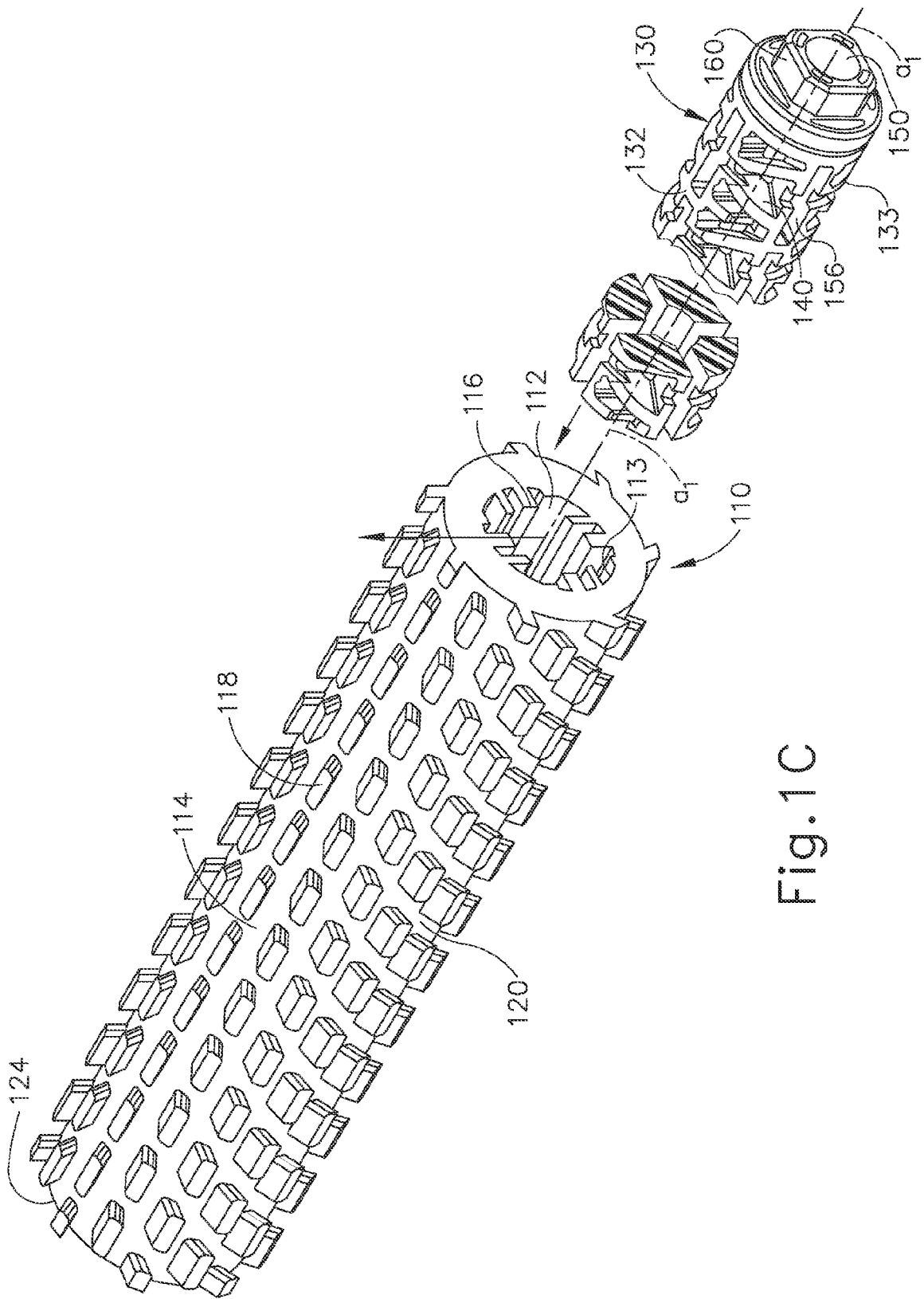

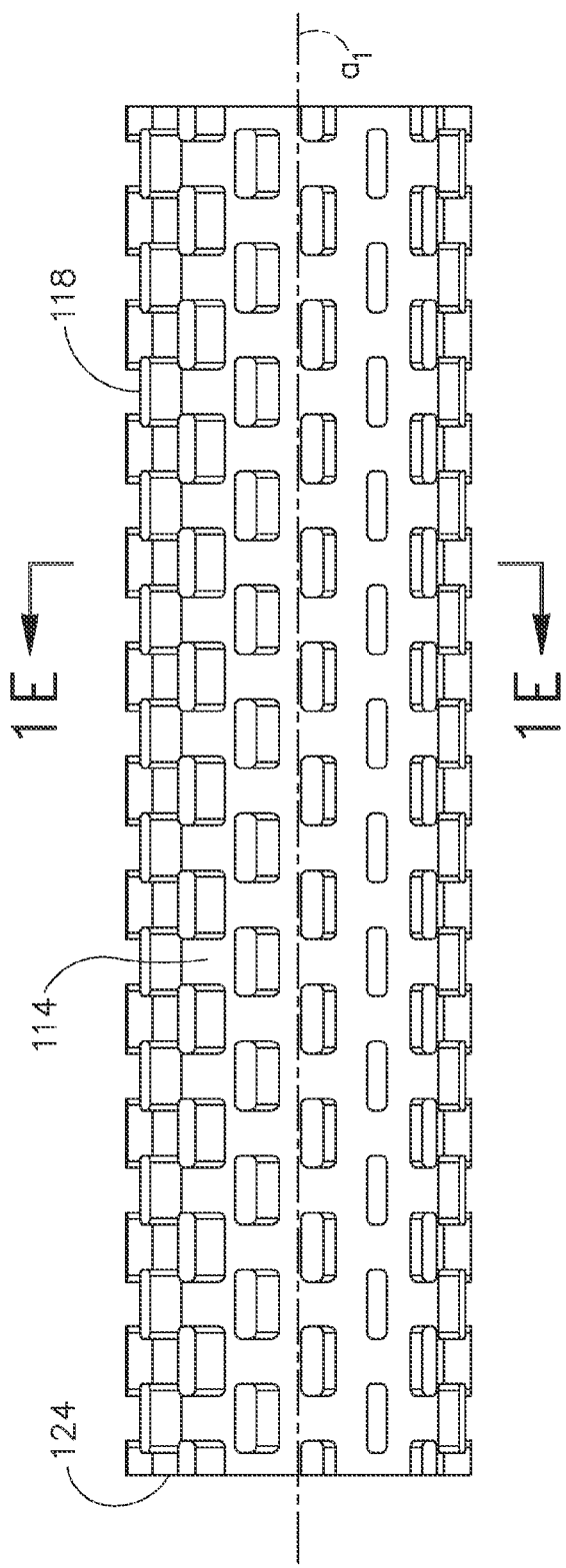
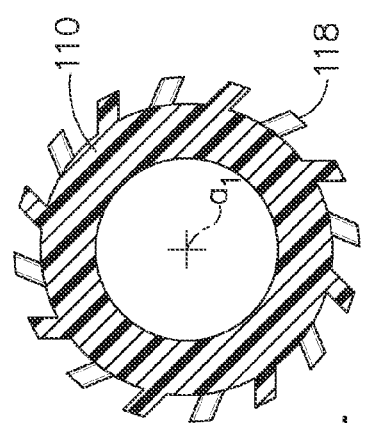
Fig. 1D
Fig. 1E

BRUSH WITH CANTILEVERED NODULES

BACKGROUND

Cast cylindrical brushes, also known as cleaning brushes, are cleaning brushes usually made of polyvinyl alcohol (PVA) and conventionally used in automatic cleaning systems to provide a post CMP (Chemical Mechanical Planarization) process to effectively clean surfaces of substrates such as semiconductor wafers or other disc-shaped substrates. Cleaning brushes are also used in cleaning systems to clean and dry glass and other non-disc-shaped substrates in flat panel display manufacture, glass production, and printed circuit board assembly. Cleaning brushes preferably have a length as short as 50 millimeters or as long as 10 meters, for example.

The cleaning brushes are located on and driven by a central brush core in the cleaning process. An accurate and stable connection between the cleaning brush and the central brush core is desirable. The cleaning brushes may have nodules on their outer surface to help clean the substrate.

The cleaning brushes are expected to accurately rotate on their axis and provide a generally cylindrical surface with a generally consistent nodule pressure pattern over their useful life, which defines optimum cleaning of the entire substrate surface in the least amount of time with minimal damage to the substrate surface. In some cases, the cleaning brush is formed around the central brush core. For example, the brush core may be placed in a mold and a mixture of chemicals comprising one or more polymer precursors, such as vinyl alcohol, is injected into the mold to form the cleaning brush around the central brush core.

Traditional cleaning brushes feature nodules, typically cylindrical, that protrude perpendicularly from the body of the brush (FIGS. 1A-1B). Under typical operating conditions necessary for proper cleaning of the semiconductor surface after CMP, traditional brush nodules generate excessive shear force since they protrude perpendicularly from the body of the brush. As a result, the excessive shear force, along with an excessive normal force, adversely affects the exposed surfaces to be cleaned by generating mechanically induced defects, like scratches. Scratches generated by the cleaning brush adversely affect the performance, yield, and reliability of the semiconductor device.

As a result, it would be desirable to have a cleaning brush in which fewer particles may get trapped between the cleaning brush and the substrate. Additionally, it would also be desirable to have a cleaning brush in which the shear force and the normal force applied onto the substrate from the cleaning brush is reduced, resulting in less mechanically induced defects generated by the cleaning brush.

SUMMARY

In one aspect, the present invention provides a cleaning device for cleaning substrates. The device comprises: a cleaning brush having an outer cleaning surface surrounding a hollow bore and positioned around a first central axis $a_1$ defining a first rotational direction $\alpha$; and a plurality of cantilevered nodules formed on the outer cleaning surface, a plurality of cantilevered nodules formed on the outer cleaning surface. Each nodule has a mounting portion connected with the outer cleaning surface, a cleaning portion connected with the mounting portion, and a contact member for engaging the substrate. The cleaning portion extends in a first direction $D_1$ from the mounting portion to the contact member, wherein a radial direction $D_r$ is defined as extending radially from the central axis $a_1$ towards the outer cleaning surface and normal to the rotational direction $\alpha$, and wherein the first direction $D_1$ intersects with the radial direction $D_r$ at an angle $\gamma$.

In a second aspect, the present invention provides a method for cleaning substrates. The method comprises engaging a substrate with a cleaning device, the cleaning device including: a cleaning brush having an outer cleaning surface surrounding a hollow bore and positioned around a first central axis $a_1$ defining a first rotational direction $\alpha$; and a plurality of cantilevered nodules formed on the outer cleaning surface, each nodule having a mounting portion connected with the outer cleaning surface and a cleaning portion connected with the mounting portion and having a contact member for engaging the substrate. The cleaning portion extends in a first direction $D_1$ from the mounting portion to the contact member, wherein a radial direction $D_r$ is defined as extending radially from the central axis $a_1$ towards the outer cleaning surface and normal to the rotational direction $\alpha$, and wherein the first direction $D_1$ intersects with the radial direction $D_r$ at an angle $\gamma$. The brush is then rotated about first central axis $a_1$ in first rotational direction $\alpha$.

In a third aspect, the present invention provides a cleaning device for cleaning substrates. The device comprises: a cleaning brush having an outer cleaning surface surrounding a hollow bore and positioned around a first central axis $a_1$ defining a first rotational direction $\alpha$; and a plurality of cantilevered nodules formed on the outer cleaning surface, each nodule having a mounting portion connected with the outer cleaning surface and a cleaning portion connected with the mounting portion and having a contact member for engaging the substrate, the contact member having an outer end surface connected with a side surface of the cleaning portion, wherein the outer end surface is positioned so that only a portion of the outer end surface engages the substrate during a cleaning of the substrate.

The scope of the present invention is defined solely by the appended claims and is not affected by the statements within this summary.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 1A depicts a traditional cleaning brush having nodules that protrude perpendicularly from the body of the brush.

FIG. 1B depicts a cross-sectional view along line 1B of the cleaning brush depicted in FIG. 1A.

FIG. 1C depicts a partially exploded perspective view of a cleaning brush having cantilevered nodules and brush core, in accordance with one embodiment of the present invention.

FIG. 1D depicts a side view of a cleaning brush having cantilevered nodules, in accordance with one embodiment of the present invention.

FIG. 1E depicts a cross-sectional view along line 1E of the cleaning brush depicted in FIG. 1D.

DETAILED DESCRIPTION

Figure 2:
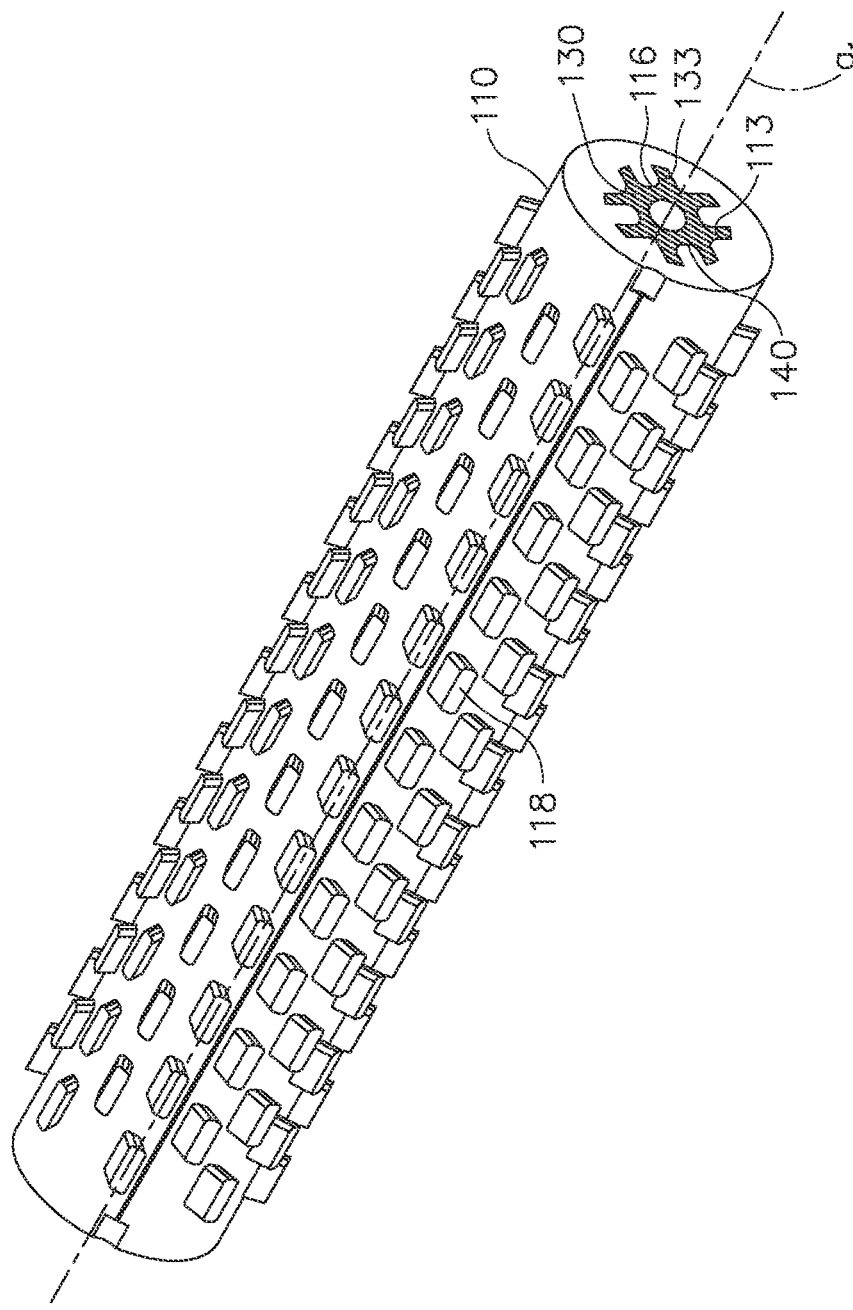
FIG. 2 depicts a perspective view of a cleaning brush having cantilevered nodules and brush core, in accordance with one embodiment of the present invention.

Methods and systems consistent with the present invention overcome the disadvantages of conventional brushes and brush-core systems by forming a cleaning brush having cantilevered nodules, resulting in reduced pressure between the cleaning brush and the substrate being cleaned at an engagement area along which the cleaning brush engages the substrate. The cantilevered nodules provide the proper surface contact required for efficient surface but reduce the applied shear force delivered to the semiconductor wafer. As a result, by using cantilevered nodules the frequency and magnitude of mechanically induced defects may be reduced, and the overall performance, yield, and reliability of the semiconductor device may be improved. Without being bound to any particular theory, having a cantilevered geometry allows the nodules to comply, or bend, when pressed against a substrate, instead of being compressed when pressed against the substrate, thereby reducing a delivered shear force on the substrate.

With reference to FIGS. 1C-3, there is shown a cleaning system 100 for cleaning and polishing substrates 104. Preferably, the cleaning system 100 is an automatic cleaning system which can automatically or manually be set to polish and/or clean a substrate 104, and more particularly a surface 106 of the substrate 104. Substrate 104 includes any one of a variety of circular, disc-shaped or non-disc-shaped substrates, such as: silicon based substrates including glass, dry glass, semiconductor wafers, flat panel display glass panels, glass production panels, and printed circuit boards; polymer-based substrates; and various types of semiconductor substrates such as silicon-based semiconductor substrates, single element semiconductor substrates, silicon on insulator (SOI) substrates, III-V semiconductor substrates, II-VI semiconductor substrates, other binary semiconductor substrates, ternary semiconductor substrates, quaternary semiconductor substrates; fiber optic substrates; superconducting substrates; glass substrates; fused quartz substrates; fused silica substrates; epitaxial silicon substrates; copper substrates; and organic semiconductor substrates.

Cleaning system 100 includes a cleaning brush 110 having a hollow bore 112, a brush core 130 engaging the brush 110 within the hollow bore 112, and a rotational device 102 engaging the brush core 130. The cleaning brush 110 may be any brush which is or may be conventionally used in an automatic cleaning system to provide a post chemical mechanical planarization (CMP) process to effectively clean the surface 106 of substrate 104, such as a cast polyvinyl alcohol (PVA) foam brush, a polyurethane foam brush, or other polymeric foam brush. Preferably, the cleaning brush 110 is generally frusto-conically shaped, conically-shaped, or cylindrically-shaped.

As defined herein, a generally conically-shaped member, or a generally frusto-conically shaped member, such as the brush 110, is a member which is formed around a longitudinal central axis $a_1$, which is preferably balanced around the central axis $a_1$ in such a way that the centrifugal forces generated by the member as the member rotates around the central axis $a_1$ vary by no more than ±20%, providing for a relatively balanced member, and for which one end has a greater cross-sectional area, when taken perpendicular to the central axis $a_1$, than a second end. As a result, a generally conically-shaped member, or a generally frusto-conically shaped member does not have to have a perfectly smooth outer surface, but can have interruptions, such as nodules or cavities formed on or in its outer surface. As defined herein, a generally cylindrically-shaped member, such as the brush 110, is a member which is formed around a longitudinal central axis $a_1$, and which is preferably balanced around the central axis $a_1$ in such a way that the centrifugal forces generated by the member as the member rotates around the longitudinal central axis $a_1$ vary by no more than ±20%, providing for a relatively balanced brush 110. As a result, the brush 110 does not have to have a perfectly cylindrical outer surface 110, but can have interruptions, such as nodules or cavities formed on or in its outer surface.

With reference to FIG. 1, the cleaning brush 110 includes an outer cleaning surface 114 opposed to an inner surface 113, forming the hollow bore 112. The hollow bore 112 may be formed around the brush core 130, preferably by injection molding the brush 110 around an already formed brush core 130 or the hollow bore 112 may be formed and then later placed around the brush core 130. The hollow bore 112 is defined by the inner surface 113 of the conically-shaped brush 110. In one embodiment, the inner surface 113 is interrupted by a second engagement member 116 which mates with and surrounds a first engagement member 140 of the brush core 130. By forming the second engagement member 116 around the first engagement member 140, the brush 110 is securely fitted to the brush core 130 in order to prevent slippage and movement between the brush core 130 and the brush 110.

With reference to FIGS. 1C-1E, outer cleaning surface 114 includes cantilevered nodules 118 formed on or in the outer cleaning surface 114. Having surface features such as nodules 118 may help brush 110 to better clean certain substrates 104 with less scratching.

With reference to FIG. 2, the brush core 130 engages the brush 110 within the hollow bore 112. The brush core 130 includes a body section 132 which forms an outer surface 133 which engages and is preferably secured to the inner surface 113 defining the hollow bore 112 of the brush 110. In one embodiment, the brush core 130 is generally conically-shaped, or generally frusto-conically shaped. In one embodiment, the brush core 130 is generally cylindrically shaped.

Figure 3:
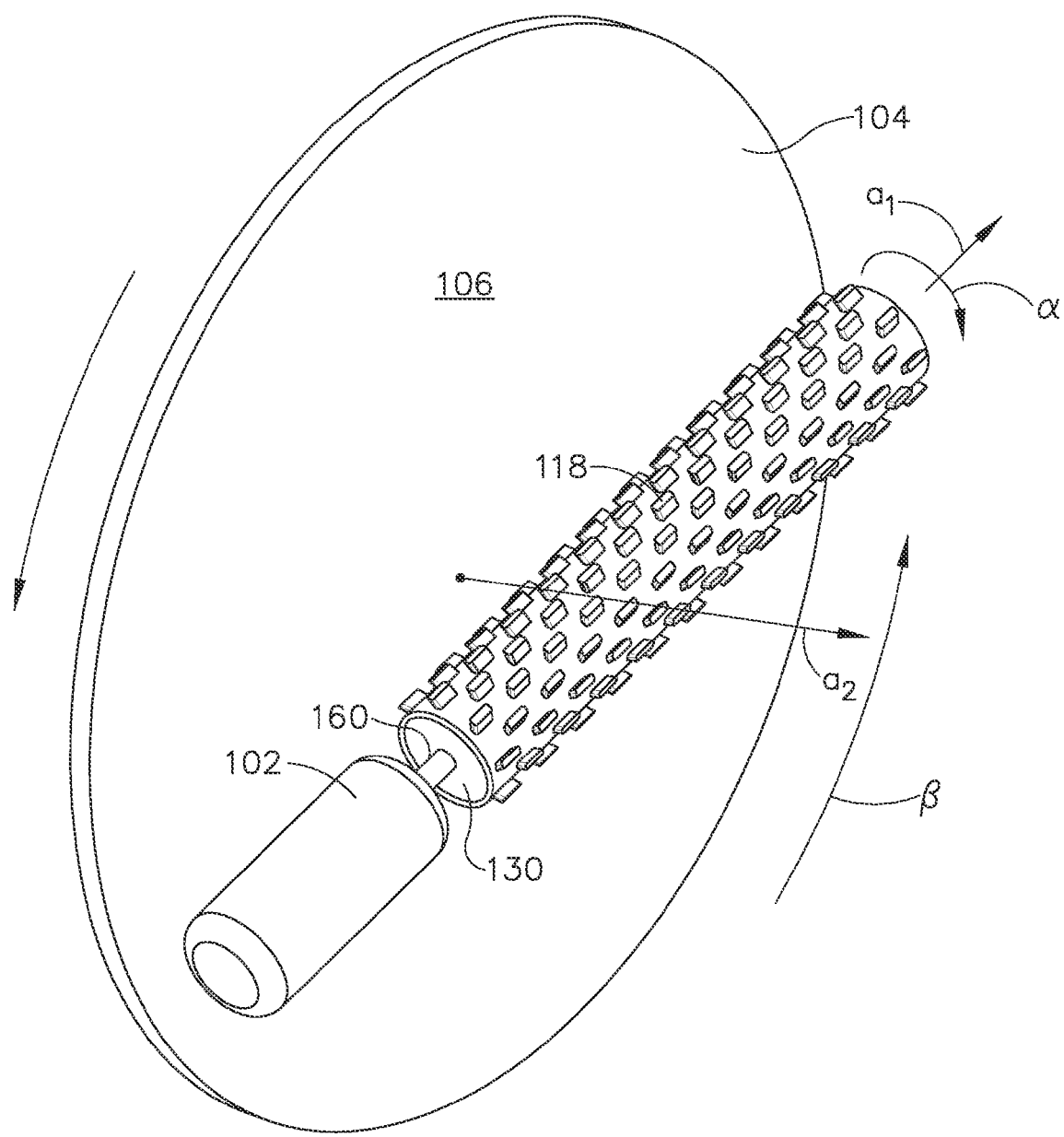
FIG. 3 depicts a perspective view of a cleaning system for cleaning and polishing substrates, in accordance with one embodiment of the present invention.

With further reference to FIG. 2, preferably, outer surfaces 114 and 133 are positioned about the longitudinal central axis $a_1$ of the brush core 130, and more preferably, the outer surfaces 114 and 133 are positioned symmetrically about the central axis $a_1$ of the brush core 130. In order to prevent rotational movement, and preferably axial movement, between the brush 110 and the brush core 130, the profile or contour of the outer surface 133 may be interrupted by a first engagement member 140. Rotational movement is defined herein as movement along a rotational direction α about the central axis $a_1$, as shown in FIG. 3. Axial movement is defined herein as movement along an axial direction which is generally perpendicular to, within ±30 degrees of the central axis $a_1$. First engagement member 140 is any feature which interrupts the general contour of outer surface 133 in order to better engage the second engagement member 116 of the brush 110. First engagement member 140 includes such features as a band or a series of bands, a ridge or series of ridges, or a channel or a series of channels at any number of locations along the outer surface 133 to effectively axially secure the brush 110 to the brush core 130.

As a result of first and second engagement members 140, 116, the physical fit between the outer surface 133 of the brush core 130 and the inner surface 113 of the brush 110 provides significant resistance to slipping. This resistance to slipping could be further enhanced by other methods including adhesives, surface preparation of the core (chemical, physical, corona, and the like), or such additional surface features as knurls, sharp edges, hooks, points, keys, or other linking features.

With reference to FIGS. 4B-4E, brush 110 features cantilevered nodules 118. Cantilevered nodules 118 experience some amount of tensile force at a first end due to a load at a second end. Cantilevered nodule 118 is projecting above the outer cleaning surface 114, is connected to the outer cleaning surface by a mounting portion 1180, and carries a load at a cleaning portion 1182 opposite the mounting portion 1180. The cantilevered nodule 118 also experiences tensile force and very little if any compressive force at the mounting portion 1180. The cleaning portion 1182 extends from the mounting portion 1180 in a direction $D_1$ to a contact member 1184 for engaging the substrate. Example cantilevered nodules 118 can be tilted or slanted (as in FIG. 4B), L-shaped (as in FIG. 4C), curved (as in FIG. 4D), or V-shaped (as in FIG. 4E).

Figure 4A:
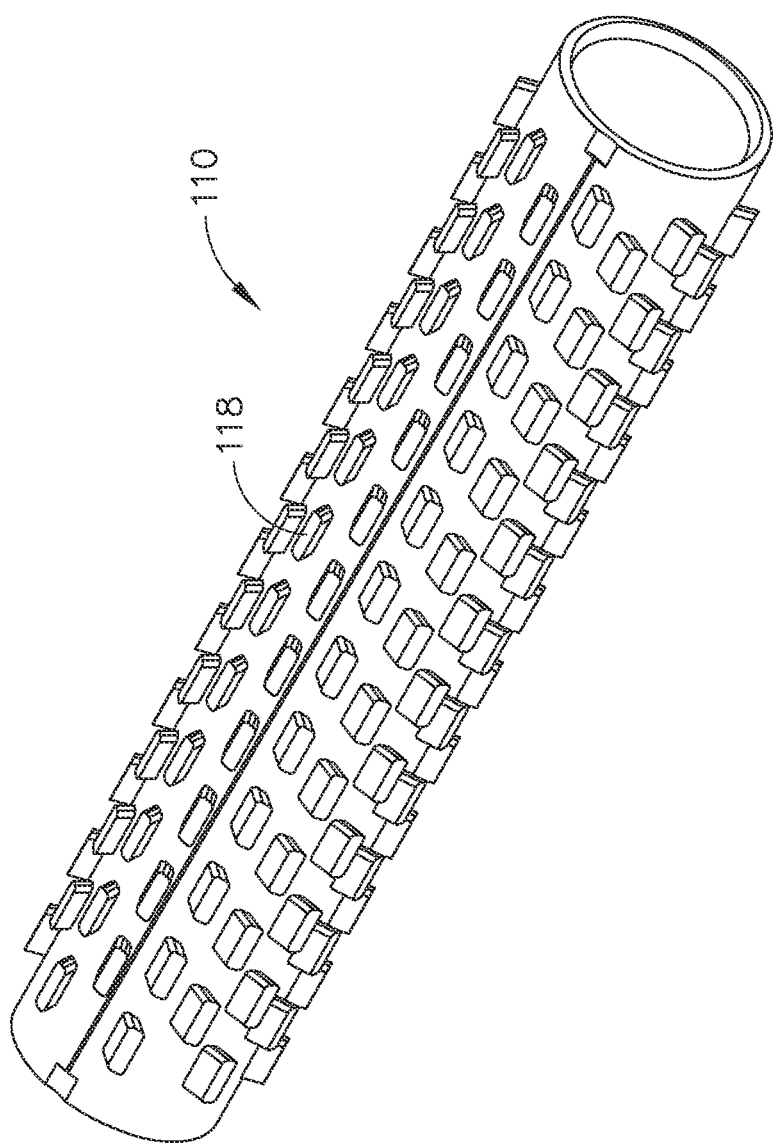
FIG. 4A depicts a perspective view of the cleaning brush having cantilevered nodules, in accordance with one embodiment of the present invention.
Figure 4C:
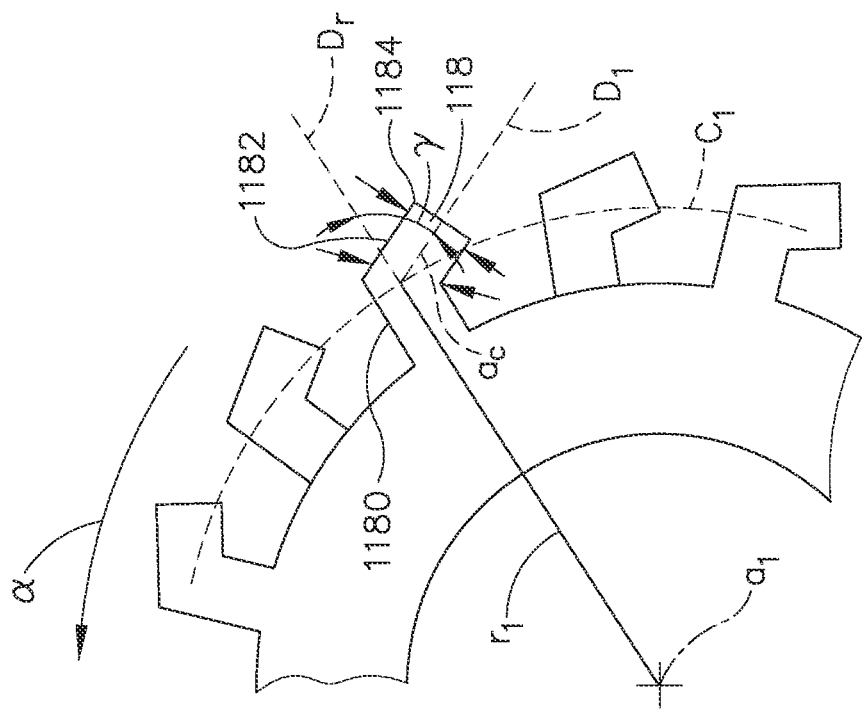
FIG. 4C depicts a cross-sectional view along line C-C of a cleaning brush having cantilevered nodules where the nodules are L-shaped, in accordance with one embodiment of the present invention.
Figure 4B:
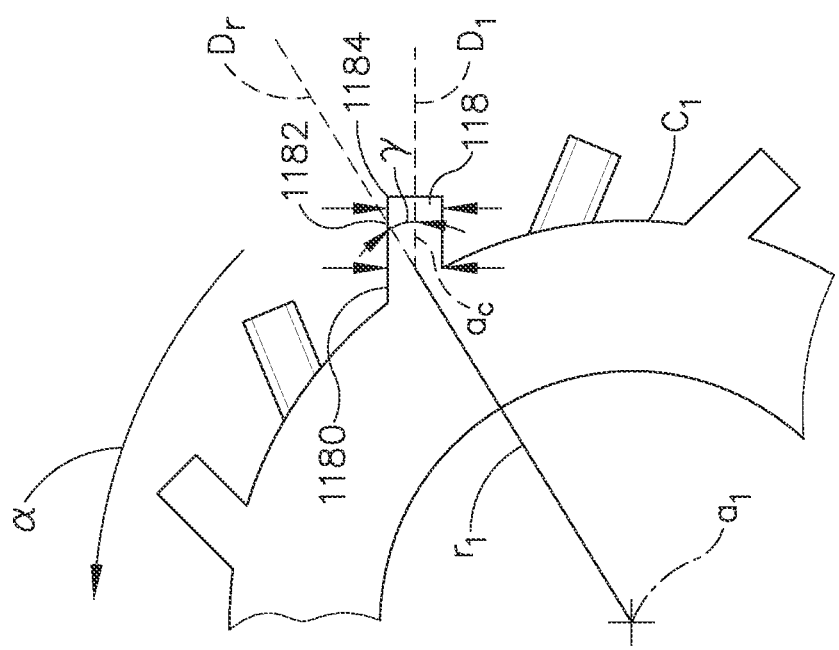
FIG. 4B depicts a cross-sectional view along line C-C of a cleaning brush having cantilevered nodules where the nodules are cantilevered, in accordance with one embodiment of the present invention.
Figure 4E:
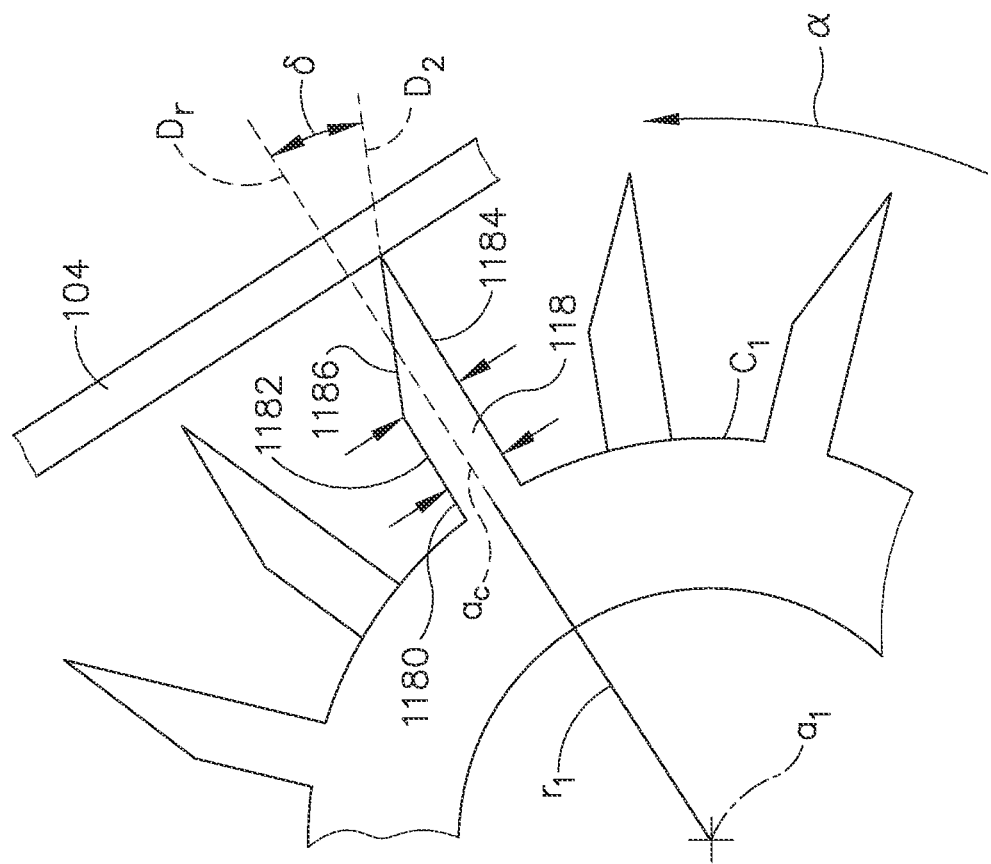
FIG. 4E depicts a cross-sectional view along line C-C of a cleaning brush having cantilevered nodules where the nodules are V-shaped, in accordance with one embodiment of the present invention.
Figure 4D:
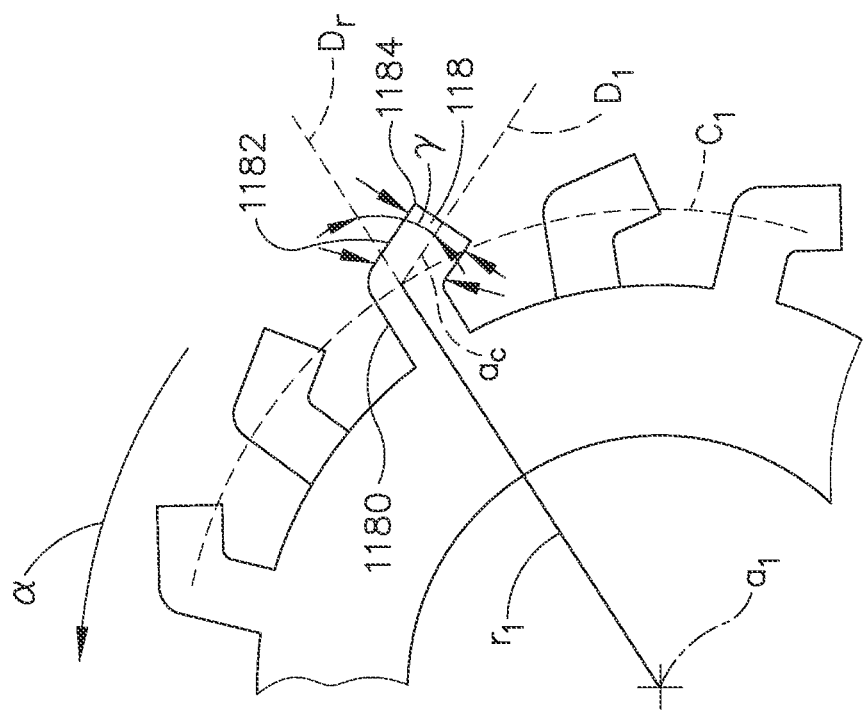
FIG. 4D depicts a cross-sectional view along line C-C of a cleaning brush having cantilevered nodules where the nodules are curved, in accordance with one embodiment of the present invention.

With reference to the example nodules 118 of FIGS. 4B-4D, direction $D_1$ of the cleaning portion 1182 forms an angle γ with radial direction $D_r$, where direction $D_r$ is from the central axis $a_1$ towards and normal to the rotational direction α about the central axis $a_1$. Direction $D_1$ can be defined as that of axis $a_c$, a segment drawn through the geometrical center of the cross-section of 118. Circle $c_1$ lies in a plane perpendicular to central axis $a_1$ and is centered on axis $a_1$; a point traveling on the perimeter of $c_1$ thus moves in rotational direction α. Circle $c_1$ is of radius $r_1$, where $r_1$ extends in radial direction $D_r$ and the length of $r_1$ is the shortest distance between axis $a_1$ and axis $a_c$. In the example nodules of FIGS. 4B-4C, direction $D_1$ intersects direction $D_r$ at an angle γ, so nodule 118 can be defined as being tilted by an angle γ from the normal to the rotational direction α about the central axis $a_1$. Angle γ is greater than 0° and less than 180°. Preferably, γ is at least ±10 degrees and at most ±90 degrees. More preferably, γ is at least ±20 degrees to at most ±70 degrees. Most preferably, γ is at least ±30 degree to at most ±60 degrees. In the alternative, preferably, the cleaning axis $a_c$ does not intersect with the central axis $a_1$. As a result, nodules 118 do not extend out radially from the central axis $a_1$.

With reference to the example curved nodule 118 of FIG. 4D, as a result of the curvature, mounting portion 1180 is generally perpendicular to cleaning surface and the direction $D_1$ of cleaning portion 1182 intersects radial direction $D_r$ at an angle γ. Here, too, γ is at least ±10 degrees and at most ±90 degrees. More preferably, γ is at least ±20 degrees to at most ±70 degrees. Most preferably, γ is at least ±30 degree to at most ±60 degrees.

With reference to the example V-shaped nodule 118 of FIG. 4E, the mounting portion 1180 and cleaning portion 1182 are both perpendicular to outer cleaning surface 114, but the outer end surface 1186 of the contact member 1184 is slanted instead of parallel to the substrate 104. As a result, the outer end surface 1186 is positioned so that only a portion of the outer end surface engages the substrate during a cleaning of the substrate. As illustrated in FIG. 4E, the extent of the slant of outer surface 1186 can be measured as slant angle δ where direction $D_2$ of the outer end surface 1186 intersects with direction $D_r$ as defined above. Preferably, angle δ is at least ±10 degrees to at most ±80 degrees. More preferably, angle δ is at least ±20 degrees to at most ±70 degrees. Most preferably, angle δ is at least ±30 degrees to ±60 degrees.

Figure 5:
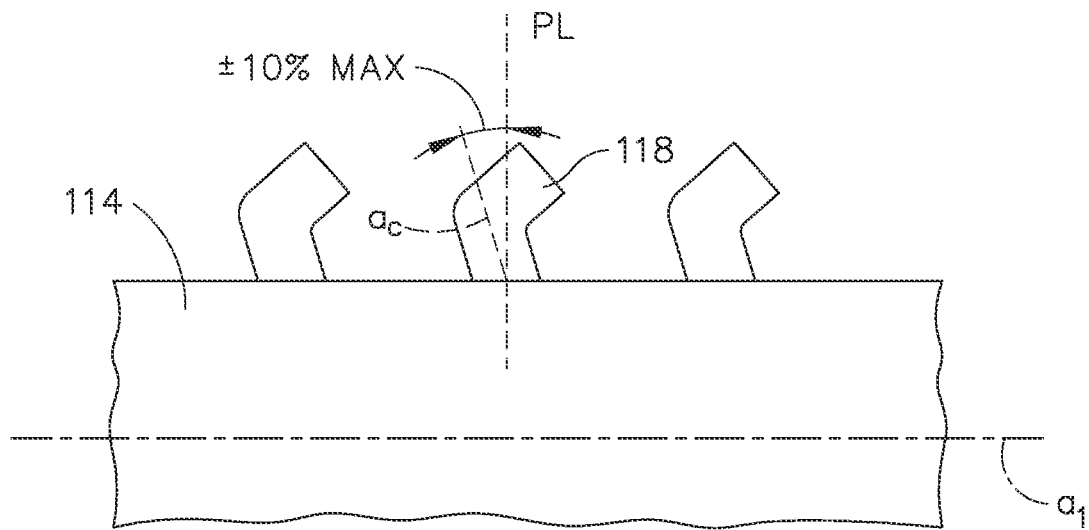
FIG. 5 depicts a side view of a cleaning brush having cantilevered nodules, in accordance with one embodiment of the present invention.

With reference to nodules 118 having a mounting portion 1180 that is perpendicular to the outer cleaning surface 114, it should be understood that perfect perpendicularity, is not required, and mounting portion 1180 may be generally but not perfectly perpendicular to the cleaning surface 114 without departing from the scope of the invention. In some embodiments, the mounting portion 1180 may be generally perpendicular to the cleaning surface 114, ±10°. With reference to FIG. 5, this may be visualized by defining a mounting portion axis $a_m$, that is, a segment drawn through the geometrical center of the cross-section of mounting portion 1180. In a preferred embodiment, axis $a_m$ is perpendicular to cleaning surface 114, ±10°.

As exemplified in FIGS. 1C-4E, nodule 118 extends directly from the cleaning surface 114. The nodules 118 are preferably characterized by a generally rectangular cross-section, and direction $D_1$ lies in a plain perpendicular to axis $a_1$. Though preferable, it is to be understood that having such geometrical features are not strict requirements, and one of ordinary skill in the art will appreciate that changes in the shape of nodule 118 may be made without departing from the scope of the invention.

Figure 6:
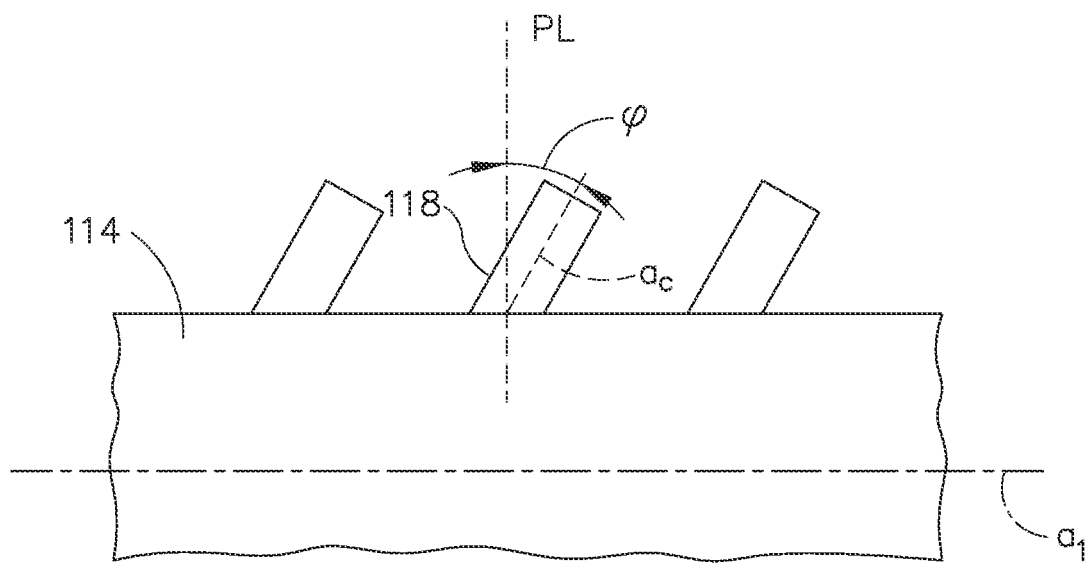
FIG. 6 depicts a side view of a cleaning brush having cantilevered nodules, in accordance with one embodiment of the present invention.

For example, and as illustrated in FIG. 6, direction $D_1$ may not lie in a plane that is perfectly perpendicular to axis $a_1$, but instead form an angle φ therewith, wherein φ is preferably within ±10 degrees. In such embodiments, angle γ is measured between radius $r_1$ and the projection of $D_1$ onto PL, a plane perpendicular to axis $a_1$. Also, the cross-section of the nodule 118 may be of a shape other than rectangular, for example tubular, elliptical or irregular.

One of ordinary skill in the art will readily appreciate that such differences from the examples of FIGS. 1C-4E are insubstantial and do not cause a departure from the scope of the invention, provided that the general direction of the cleaning portion 1182 is characterized by a cantilevered geometry, thereby resulting in a gentler cleaning action than that afforded by traditional nodules. It is also to be understood that the nodules 118 are characterized by a tilt, slant, or curvature that is permanent and not occasioned by engaging the brush with a substrate.

The nodules 118 can be manufactured in any length, width, height, and molded at any specified angle from perpendicular. Preferably, the nodules 118 are made of the same material as the cleaning brush 110, and are 1 to 10 mm in length. More preferably, the nodules 118 have a length of 4 to 8 mm, and most preferably of 5 to 7 mm.

With reference to FIGS. 1 and 3, in one embodiment the brush core 130 also includes a rotational engagement member 160 for engaging and connecting with a rotational device 102. The rotational engagement member 160 is any device which can be used to connect with or fasten to another device, and includes things such as a nut-shaped piece that is integrally formed with the brush core 130 and can be fastened to the rotational device 102. The rotational device 102 includes any device which can induce a rotational movement onto the brush core 130, such as an electrical motor, a gas motor or engine, a crank shaft power by a motor or manually powered, and any combination of pulleys, wheels, mechanical linkages, and/or gears moved automatically or manually. The rotational device 102 has a complimentary engagement member which connects with the rotational engagement member 160 for engaging and connecting the brush core 130 with the rotational device 102.

In operation, the brush 110 is placed or formed around the brush core 130, preferably by injection molding the brush 110 around the brush core 130. Upon placing or forming the brush 110 around the brush core 130, the brush core 130 and the brush 110 are then connected with the rotational device 102 by connecting the rotational engagement member 160 with an engagement member on the rotational device 102. Then, the brush 110 is rotated along the rotational direction a about the central axis $a_1$. While rotating the brush 110, or before rotating the brush 110, the brush 110 is placed near and engages the surface 106 of the substrate 104.

The brush 110 engages the substrate 104 with brush core 130 positioned about first longitudinal central axis $a_1$. Upon engaging the brush 110 with the substrate 104, the brush 110 is then rotated about the first central axis $a_1$ in first rotational direction $\alpha$ and the substrate 104 is rotated about a second central axis $a_2$ in a second rotational direction $\beta$. Preferably, the second central axis $a_2$ is either perpendicular to or intersects the first central axis $a_1$.

Figure 7:
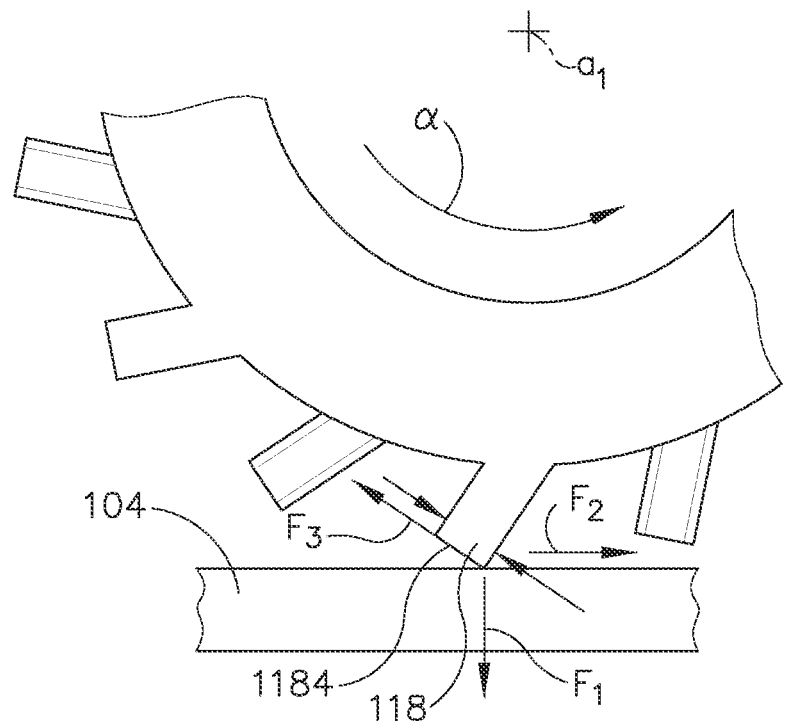
FIG. 7 depicts a cross-sectional view of a cleaning brush having cantilevered nodules, in accordance with one embodiment of the present invention, as it engages a substrate.
Figure 8:
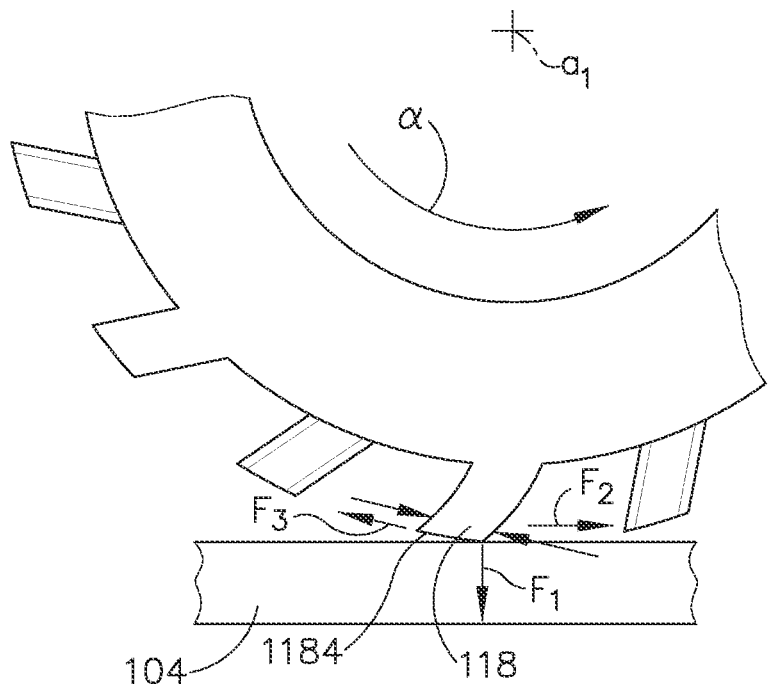
FIG. 8 depicts a cross-sectional view of a cleaning brush depicted in FIG. 7, as a cantilevered nodule bends as a result of contacting the substrate.

With reference to the example embodiment of FIG. 7, the contact member 1184 of a cantilevered nodule 118 according to the invention engages the substrate 104 with a first compressive force $F_1$ normal to the substrate 104 and a second shear force $F_2$ parallel to the substrate 104. As set forth above, the nodules 118 in the brush 110 are characterized by the cantilevered configuration described above before the brush 110 is pressed against the substrate 104, when the brush 110 and the nodules 118 are not engaged with the substrate 104. Upon engagement of the brush 110 with the substrate 104, the nodules 118 are allowed to comply, or bend, as illustrated in FIG. 8, and undergo very little if any compression at the mounting portion 1180 when the brush 110, and specifically the contact member 1184, is applied against the substrate 104.

By using a cantilevered nodule 118, the compressive force $F_1$ and shear force $F_2$ applied to the substrate 104 may be substantially reduced. The compressive force $F_1$ and shear force $F_2$ applied to substrate 104 are also transferred to the mounting portion 1180 of the nodule 118 as essentially a nodule force $F_3$ having a large tensile or shear component and having a substantially reduced and nearly eliminated compressive force component. In one embodiment, the compressive force component of the nodule force $F_3$ is less than 10% of the entire nodule force $F_3$ transferred to the nodule 118.

Figure 9A:
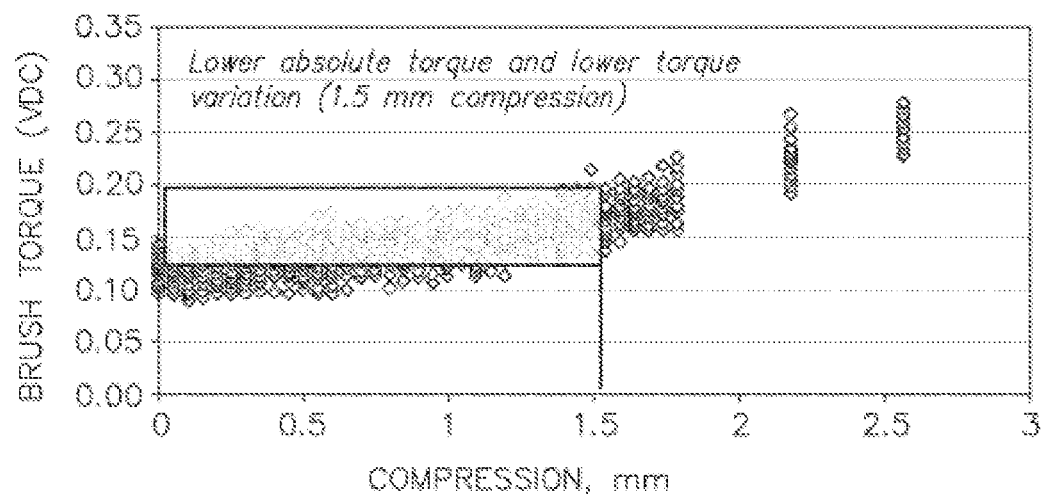
FIG. 9A illustrates the dependence of brush torque on brush compression in a traditional brush.
Figure 9B:
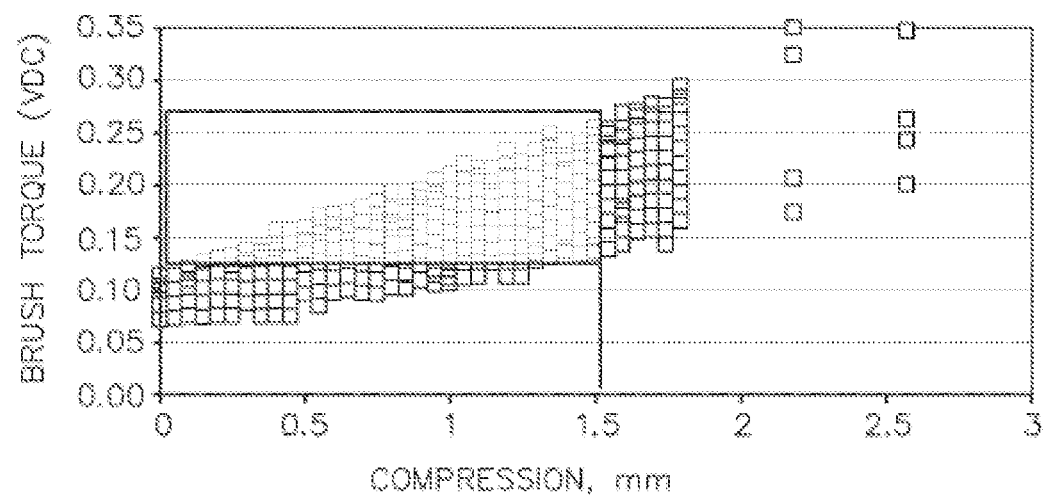
FIG. 9B illustrates the dependence of Brush Torque on Compression in an example brush having cantilevered nodules in accordance with the present invention.
Figure 9C:
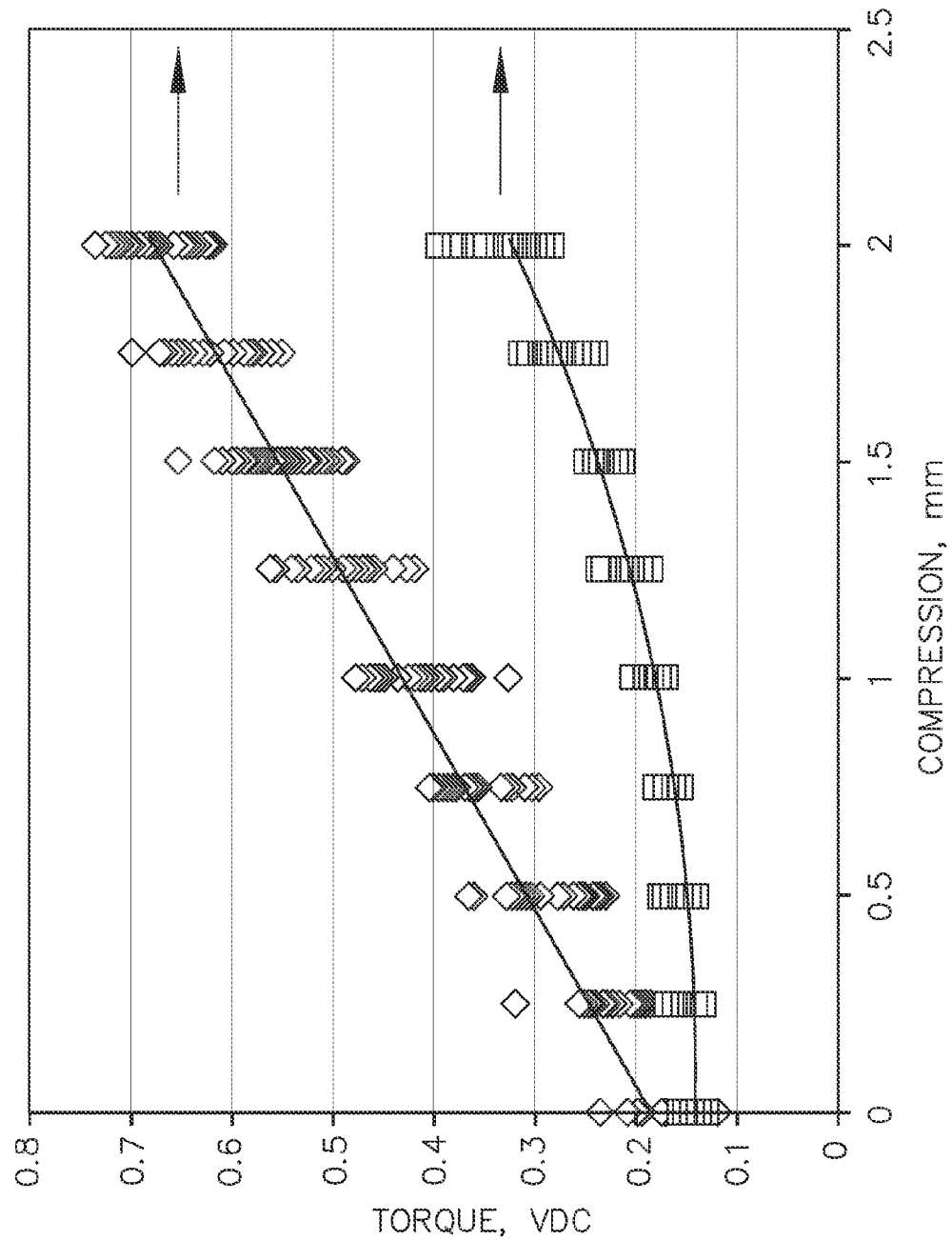
FIG. 9C illustrates a comparison of the dependence of Brush Torque on Compression in a traditional brush (diamonds) and in a brush in accordance with the present invention (squares).
Figure 10:
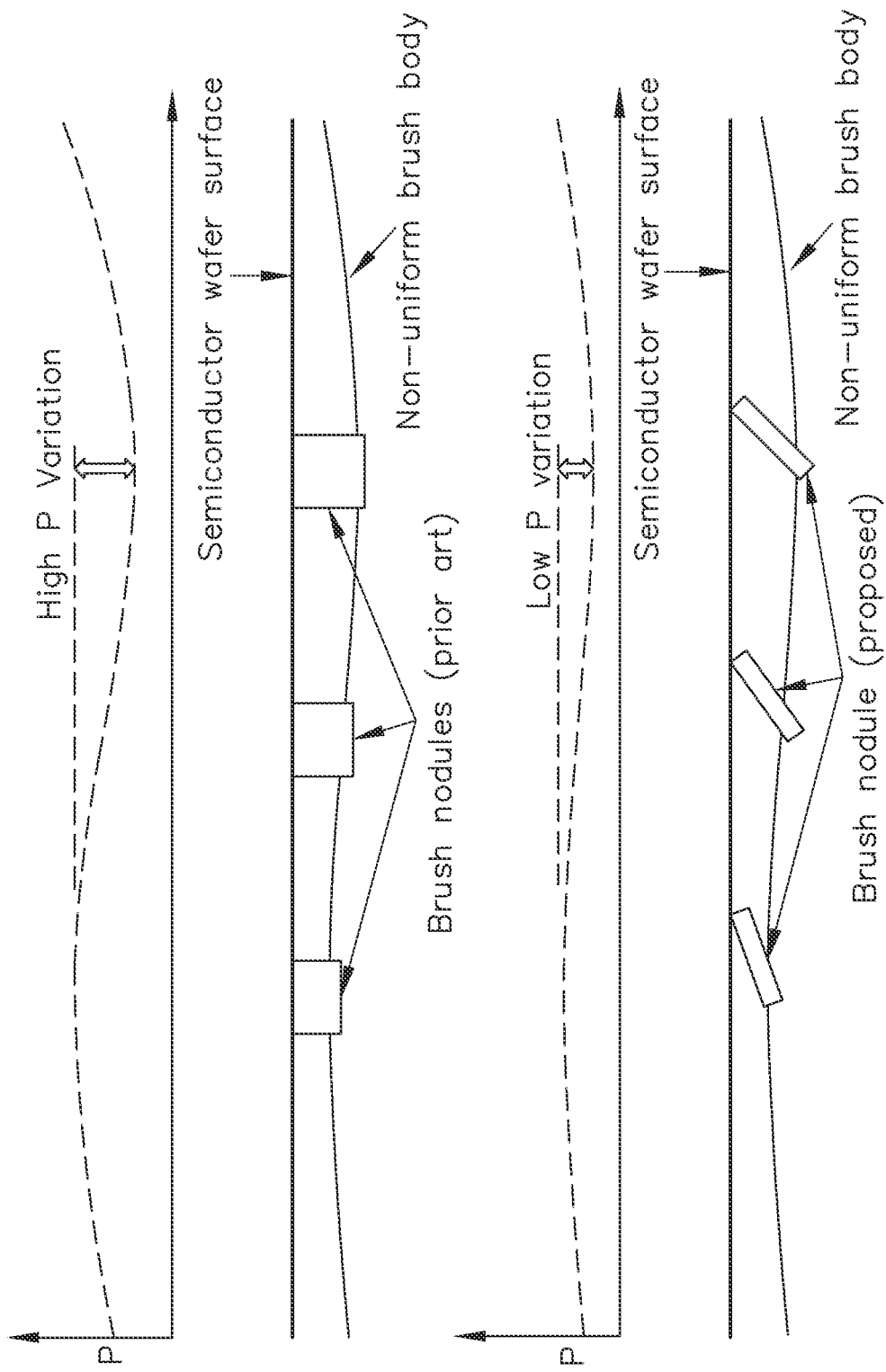
FIG. 10 illustrates compares the pressure variation attained with a traditional brush (upper graph) to that attained with a brush according to the present invention (lower graph).

The reduction in shear force $F_2$ applied to the substrate 104 may be measured by plotting the torque response of the servo motor commonly used to rotate the brush 110 around axis $a_1$ versus the extent of compression against the surface being brushed. As illustrated in FIGS. 9A-9C, lower absolute torque and lower torque variations are produced as compared to traditional brushes featuring straight, un-cantilevered nodules. As illustrated in FIG. 10, because brush-surface contact is also inherently non-uniform, the cantilevered nodule 118 also normalizes the pressure distribution of the brush on the surface, thereby lowering torque variation and reducing the contact pressure where the compression of the cleaning brush 110 needs to be increased to compensate for brush non-uniformity effects.

The rotational motion of the brush 110 on the surface 106 helps to clean and/or polish the surface 106. With reference to FIG. 3, one embodiment is shown where the substrate 104 is also rotated along rotational direction $\beta$ about second central axis $a_2$. In one embodiment, polishing fluid is pumped through fluid channel 150 formed in the body section 132 and into the brush 110 through pores 156 formed through the outer surface 133 of the body section 132 and to the fluid channel 150. The polishing fluid helps to further clean and/or polish the substrate 104.

Although the illustrative examples above describe PVA brushes 110 used to clean semiconductor substrates 104, one having skill in the art will appreciate that methods and systems consistent with the present invention are not limited thereto. For example, the brush 110 may include other materials and may be used to clean other types of surfaces 106 or substrates 104.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

While various embodiments of the invention have been described, it will be apparent to those of ordinary skill in the art that other embodiments and implementations are possible within the scope of the invention. Accordingly, the invention is not to be restricted except in light of the attached claims and their equivalents.

The invention claimed is:

1. A cleaning system for cleaning substrates having a generally flat surface and an edge, the system comprising:
    a cleaning brush having an outer cleaning surface surrounding a hollow bore and positioned around a first central axis $a_1$ defining a first rotational direction $\alpha$, wherein the first central axis $a_1$ is oriented substantially parallel to the flat surface of the substrate for cleaning the flat surface of the substrate;

a plurality of cantilevered nodules formed on the outer cleaning surface, each nodule having a mounting portion connected with the outer cleaning surface, a cleaning portion connected with the mounting portion, and a contact member for engaging the flat surface of the substrate;

a rotational device coupled to the cleaning brush for rotating the cleaning brush about the first central axis $a_1$; and a rotational engagement member coupled between the rotational device and the cleaning brush, wherein the rotational engagement member is rotatable by the rotational device to rotate the cleaning brush;

wherein the cleaning portion extends in a first direction $D_1$ from the mounting portion to the contact member, wherein a radial direction $D_r$ is defined as extending radially from the central axis a1 towards the outer cleaning surface and normal to the rotational direction α, and wherein the first direction $D_1$ intersects with the radial direction $D_r$ at an angle γ, wherein the angle γ is greater than 0° and less than 180°.

2. The cleaning system of claim 1, wherein angle γ is at least ±10 degrees and at most ±90 degrees.

3. A cleaning system for cleaning substrates, the system comprising:

a cleaning brush having an outer cleaning surface surrounding a hollow bore and positioned around a first central axis a1 defining a first rotational direction α;

a plurality of cantilevered nodules formed on the outer cleaning surface, each nodule having a mounting portion connected with the outer cleaning surface, a cleaning portion connected with the mounting portion, and a contact member for engaging the substrate;

a rotational device coupled to the cleaning brush for rotating the cleaning brush about the first central axis $a_1$; and a rotational engagement member coupled between the rotational device and the cleaning brush, wherein the rotational engagement member is rotatable by the rotational device to rotate the cleaning brush;

wherein the cleaning portion extends in a first direction $D_1$ from the mounting portion to the contact member, wherein a radial direction $D_r$ is defined as extending radially from the central axis $a_1$ towards the outer cleaning surface and normal to the rotational direction α, and wherein the first direction $D_1$ intersects with the radial direction $D_r$ at an angle γ;

wherein angle γ is at least ±20 degrees to at most ±70 degrees.

4. The cleaning system of claim 1, wherein angle γ is at least ±30 degree to at most ±60 degrees.

5. The cleaning system of claim 1, wherein first direction $D_1$ intersects with the radial direction $D_r$ at an angle γ when the brush is not engaged with a substrate.

6. The cleaning system of claim 1, wherein the nodules are characterized by a substantially rectangular cross-section.

7. The cleaning system of claim 1, wherein the mounting portion is perpendicular to the cleaning surface, ±10 degrees.

8. The cleaning system of claim 1, wherein the cleaning brush is generally conically-shaped, generally frusto-conically shaped or generally cylindrically-shaped.

9. The cleaning system of claim 1, wherein the nodules comprise a polymeric material selected from the group consisting of PVA, polyurethane, and mixtures thereof.

10. The cleaning system of claim 1, wherein the mounting portion extends in the radial direction $D_r$.

* * * * *